United States Patent [19]

Reuter et al.

[11] Patent Number: 4,835,186

[45] Date of Patent: * May 30, 1989

[54] SPRAY DRIED IBUPROFEN

[75] Inventors: Gerald L. Reuter, Plattsburgh, N.Y.; Maureen M. Harrison, St. Albans, Vt.

[73] Assignee: American Home Products Corporation, New York, N.Y.

[*] Notice: The portion of the term of this patent subsequent to May 30, 2006 has been disclaimed.

[21] Appl. No.: 62,733

[22] Filed: Jun. 15, 1987

[51] Int. Cl.[4] .............................................. A61K 31/74
[52] U.S. Cl. .................................... 514/570; 514/974; 424/499
[58] Field of Search ................. 424/499; 514/974, 570

[56] References Cited

U.S. PATENT DOCUMENTS

| 4,569,937 | 2/1986 | Baker et al. | 514/282 |
| 4,681,897 | 7/1987 | Brand | 514/557 |
| 4,695,591 | 9/1987 | Hanna | 514/781 |
| 4,726,966 | 2/1988 | Kawashima et al. | 514/974 |

FOREIGN PATENT DOCUMENTS 0190826  8/1986  European Pat. Off. ............ 514/974

Primary Examiner—Joseph L. Schofer
Assistant Examiner—Peter F. Kulkosky
Attorney, Agent, or Firm—John W. Routh

[57] ABSTRACT

A therapeutic taste-neutral powder form of ibuprofen obtained by spray-drying a suspension of colloidal silica in a lower alkanol solution of ibuprofen and cellulose acetate phthalate.

6 Claims, No Drawings

SPRAY DRIED IBUPROFEN

BACKGROUND OF THE INVENTION (a) Field of the Invention

This invention relates to a novel therapeutic form of spray dried ibuprofen having a neutral taste which can be formulated into, for example, chewable tablets and fast dissolving dosage forms as described in U.S. Pat. Nos. 4,305,502 and 4,371,516. More specifically this invention relates to a taste-neutral spray dried powder formed by spray drying a solution of ibuprofen and cellulose acetate phthalate in a mixture of a lower alkanol and ethyl acetate having suspended therein colloidal silica or montmorillonite clay. By taste-neutral it is meant that the powder has essentially no taste and is neither sweet nor bitter.

(b) Prior Art

Ibuprofen, a widely used analgesic and antipyretic, is not palatable enough to be used in chew-type tablets for those people who do not swallow whole solid-type dosage forms.

The use of flavor agents eg. chocolate, banana, orange, lemon, licorice, root beer, and raspberry, in particular, have been proposed for bitter tasting drugs. These agents are not dependable masking ingredients. Mint flavors can be useful in ameliorating a chalky taste parameter. Bitter properties, however, are very difficult to mask to any great extent, particularly, when they do not mimic the expected natural taste of the flavor agent.

Other properties ncluding mouthfeel also need to be addressed in consideration of the oral acceptance of chewable or chew-type tablets.

The fast dissolving dosage forms described in U.S. Pat. Nos. 4,305,502 and 4,371,516 are manufactured to disintegrate in water within five seconds or less and hence dissolve rapidly in the saliva of the mouth. Heretofore the use of such dosage forms were restricted to pharmaceuticals which had a neutral taste or a slightly disagreeable taste which could be masked by a flavoring agent. Pharmaceuticals with a bitter taste such as ibuprofen are not currently used in such dosage forms.

SUMMARY OF THE INVENTION

According to this invention, a novel therapeutic taste-neutral powder form of spray-dried ibuprofen is provided which can be formulated into chewable tablets and the like. The powder is formed by spray drying a solution of ibuprofen and cellulose acetate phthalate in a mixture of lower alkanol and ethyl acetate having colloidal silica suspended therein. Preferably the lower alkanol is isopropanol.

According to another aspect of this invention, a pharmaceutical dosage form for oral administration as a solid is provided, which dosage form can be disintegrated by water at 37° C. within ten seconds, and comprises as the pharmaceutical agent incorporated therein the taste neutral powder form of spray dried ibuprofen of this invention.

DETAILS OF THE INVENTION

The ibuprofen useful in this invention is the pharmaceutical grade. The cellulose acetate phthalate useful in this invention is the National Formulary or U.S.P. pharmaceutical grade.

Cellulose Acetate Phthalate is a reaction product of phthalic anhydride and a partial acetate ester of cellulose. When dried at 105° for 2 hours, it contains not less than 19.0 percent and not more than 23.5 percent of acetyl ($C_2H_3O$) groups and not less than 30.0 percent and not more than 36.0 percent of phthalyl(o-carboxybenzoyl, $C_8H_5O_3$) groups, calculated on the acid-free basis. A suitable grade is Eastman C-A-P marketed by Eastman Chemical Products, Kingsport, Tenn.

The colloidal silica useful in this invention has a high internal surface area and has a particle size of about 10 millimicrons. Suitable grades are Cabosil-M-5 marketed by Cabot Corporation of Boston, Mass., and that sold by PQ Company, Philadelphia, Pa.

The weight percent of ibuprofen in the taste neutral powder can be from about 40 to 70% by weight and the weight percent of the cellulose can range from 15% to 50% by weight. At 15% by weight of cellulose, there may be a slightly bitter taste but at 20% and above the powder is taste neutral. The weight percent of colloidal silica or clay in the taste neutral powder can be from about 5% to 40% by weight.

The solvent for the cellulose can be one of the alkanols such as methyl, ethyl, isopropyl or mixtures thereof, or a mixture with up to about 50% by volume ethyl acetate, but must be a solvent in which the ibuprofen is soluble and the celluloses are soluble or dispersible. By alcohol solutions is meant aqueous solutions.

A small amount of a hydrophobic substance such as castor oil can be added to the solution to inhibit leaching of the ibuprofen from the spray dried powder. A small amount of glyceryl monostearate can be added to improve taste masking. Plasticisers can include, in addition to castor oil, diethyl phthalate, triacetin and tributyl citrate.

Food acids, eg. fumaric acid and malic acid, which are soluble in alkanol solutions and can create an aqueous environment not greater than pH 4.0, may correct the perception of bitterness in preparing the spray dried powder.

Spray dryers can be of the usual laboratory or commercial type. Suitable spray dryers are manufactured by Buchi Laboratoriums-Technik AG, by the Anhydro Company of Attleboro, Mass. and Niro Atomizer Inc., of Columbia, Md.

The spray dryer employed in the following examples was a Buchi 190 Mini Spray Dryer. The operating conditions for the Bucci Mini Spray Drier are customarily an inlet temperature of 153° to 210° C. and a corresponding outlet temperature range of 94° to 108° C.

The following examples illustrate the formation of the taste-neutral spray dried ibuprofen powder of the invention. In these examples, cellulose acetate phthalate was obtained from Hercules Chemical Company, Wilmington, Del. It was a dry material of the standard type having a viscosity designation of 10 and an ethoxy content of 48.0% to 49.5%.

EXAMPLE I

In this example, the feed mixture to the spray dryer was composed of the following materials.

| Ingredient | Weight % Solids in powder | Grams Ingredient in suspension |
| --- | --- | --- |
| Ibuprofen, USP | 52.2 | 70 |
| Cellulose Acetate Phthalate, USP | 29.9 | 40 |
| Colloidal Silica | 14.9 | 20 |
| Ethyl acetate | — | 450 |

-continued

| Ingredient | Weight % Solids in powder | Grams Ingredient in suspension |
|---|---|---|
| Castor Oil | 2.9 | 4 |
| Isopropyl Alcohol, q.s. ad. | — | 1000 ml. |
| Total: | 100% | 1584 grams |

The ibuprofen was dissolved in a portion of the alcohol contained in a stainless steel mixing vessel with the aid of a Lightnin mixer. The cellulose acetate phthalate was dissolved in the remaining alcohol and the ethyl acetate in a separate stainless steel mixing vessel with the aid of a Lightnin mixer and then filtered. The contents of the two mixing vessels were combined. The colloidal silica was added and mixed until a homogeneous dispersion was obtained. The dispersion was than transferred to the feed hopper of the Buchi Mini Spray Dryer.

The spray drier was operated such that an air inlet temperature of 153°–210° C. and an air outlet temperature of 94° to 108° C. was maintained throughout the run.

The yield of spray dried powder was about 90% of theoretical. The product was a white, fine powder.

The freshly obtained product upon tasting and being held in the mouth for 45 seconds produced no bitterness characteristic of ibuprofen. Upon aging one month at room temperature the product remained quite acceptable without bitterness.

EXAMPLE 2

This example describes the preparation of fast dissolving dosage forms using the spray dried taste-neutral ibuprofen of Example 1 and other ingredients as follows:

| Ingredients | Weight % suspension | Grams in suspension |
|---|---|---|
| Gelatin, BY 19/50 | 4.0 | 10.00 |
| Mannitol, granular | 3.0 | 7.50 |
| Deionized water | 67.10 | 167.75 |
| NUTRASWEET, NF | 1.20 | 3.00 |
| Cherry #271 | 0.40 | 1.00 |
| Cream Flavor #59.200/A | 0.20 | 0.50 |
| Sodium lauryl sulfate | 0.10 | 0.25 |
| Croscarmellose sodium, Type A | 1.00 | 2.50 |
| Powder, Example 1 | 23.0 | 57.50 |

The procedure for preparing a batch of the above suspension takes place in two stages, i.e. the preparation of the gelatin base and the addition of the pharmaceutical agent.

The gelatin base is prepared by adding the gelatin to the deionized water at 30° C. and mixing until the gelatin is dissolved. The solution is then cooled to 25° C. and the mannitol, the sodium lauryl sulfate, the sweetener, and the flavors are separately added and dissolved.

The croscarmellose sodium in powder form (Ac-DiSol) and the taste-neutral spray dried ibuprofen powder are dry mixed and screened through a 20 mesh screen. The mixed powder is added to the gelatin solution and further admixed with a homomixer for thirty minutes to form a uniform dispersion.

The freeze drier employed in this example is a Virtis 25 SRC Model Freeze Drier. The fast dissolving dosage forms are prepared by dosing 500 milligrams of the suspension of ibuprofen into each well in a thermoformed blister tray containing 10 wells per tray. The filled trays are placed in a larger tray containing a dry ice-methanol mixture. When the suspension in the wells are frozen, the samples are placed on the freeze dryer trays at a shelf temperature of −45° C.

When the samples have reached a tempeature of −45° C., as determined by a probe in a well, the condenser is turned on and the freezer turned off. The condenser temperature is brought to between −40° and −45° C. and the vacuum is turned on to between 50 and 60 millitorrs. The heater is then turned on and the shelf temperature is adjusted to 50°–55° C. The heat-dry cycle lasts for 4 hours. The vacuum, the condenser and the heater are turned off and the samples removed. The wafters from each batch are removed from the wells in the trays. They are white in color and each weighs about 150 milligrams of which about 80 milligrams is ibuprofen. The wafers from each batch when placed on the tongue exhibit a cherry/cream flavor with a very slight bitter after taste. When placed in water at 37° C. the wafers disintegrate in less than ten seconds.

EXAMPLE 3

This example describes the preparation of a 3 gram chewable tablet using the spray dried taste neutral ibuprofen of Example 1 and other ingredients as follows:

| Ingredients | Weight |
|---|---|
| Powder of Example 1, | 1320 mg |
| Cornstarch | 200 mg |
| Mannitol | 740 mg |
| Sorbitol | 740 mg |
| Total | 3000 mg |

The powder of Example 1 contained 52.2% by weight or 689 mg of ibuprofen. The ingredients were mixed in a suitable mixer and formed into tablets using a 29 mm punch and die set on a Carver Press. Compression was accomplished at 5000 psi. The tablets when chewed in the mouth had a neutral taste and good mouthfeel. The taste could be improved by incorporation into the tablet of suitable flavoring agents such as a mint flavoring agent.

EXAMPLE 4

In this example, the feed mixture to the spray dryer was composed of the following materials.

| Ingredient | Weight % Solids in powder | Grams Ingredient per 100 ml of suspension |
|---|---|---|
| Ibuprofen, USP | 51.3 | 100 |
| Isopropyl Alcohol | — | 200 |
| Cellulose Acetate Phthalate, USP | 30.8 | 60 |
| Colloidal Silica | 12.8 | 25 |
| Castor Oil | 5.1 | 10 |
| Ethyl Acetate | — | 500 |
| Isopropyl Alcohol | — | q.s. 1000 ml. |
| Total: | 100% | |

The ibuprofen was dissolved in a 200 ml porton of the alcohol contained in a stainless steel mixing vessel with the aid of a Lightnin mixer. All was dissolved in 3 hours except for a small residue. The cellulose acetate phthalate was dissolved in a second portion of the alcohol and the ethyl acetate in a separate stainless steel mixing vessel.

After one hour mixing with the Lightnin mixer, it was completely solubilized. The contents of the two mixing vessels were then filtered and combined. The castor oil and, then the colloidal silica were added and mixed until a homogeneous dispersion was obtained. Isopropyl alcohol was then added q.s. to 1000 ml. The dispersion was then transferred to the feed tank of the Buchi Mini Spray Dryer.

The spray drier was operated such that an air inlet temperature of 153°-210° C. and an air outlet temperature of 94°-108° C. was maintained throughout the run. The freshly obtained white powder upon tasting was taste neutral.

Additional formulations were prepared essentially using the procedure of Example 1 wherein the ibuprofen and the cellulose acetate phthalate were dissolved in separate portions of alcohol, the solutions were filtered and combined and the colloidal silica and other ingredients added and stirred until a homogeneous dispersion was obtained. The mixture was stirred to maintain homogenity and spray dried at controlled temperatures and liquid feed rate to obtain a dry powder. The ingredients in these additional formulations are shown in the following Table I.

TABLE I

| | Example 5 | | Example 6 | |
|---|---|---|---|---|
| Ingredient | Grams | %* | Grams | %* |
| Ibuprofen | 100 | 47.6 | 100 | 45.5 |
| Colloidal Silica | 25 | 11.9 | 50 | 22.7 |
| Cellulose Acetate Phthalate | 60 | 28.6 | 50 | 22.7 |
| Castor Oil | — | — | 10 | 4.5 |
| Diethyl Phthalate | 25 | 11.9 | 10 | 4.5 |
| Ethyl Acetate | 500 | | 470 | |
| Isopropyl Alcohol, q.s. ad. | 1000 | | 1000 | |

*Weight percent ingredient in spray dried powder

We claim:

1. A therapeutic taste neutral powder form of spray-dried ibuprofen which consists essentially of, based upon the weight of the powder, about 40% to 70% by weight ibuprofen, about 15% to 50% by weight of cellulose acetate phthalate and about 5% to 40% by weight colloidal silica, the powder having been spray dried from a suspension of the colloidal silica in a lower alkanol solution of the ibuprofen and the cellulose material, the lower alkanol being mixed with up to 50% ethyl acetate.

2. In a pharmaceutical dosage form for oral administration as a solid, which dosage form can be disintegrated by water within ten seconds, the improvement which comprises incorporating into such dosage form as the pharmaceutical substance a therapeutic taste-neutral powder form of spray-dried ibuprofen which consists essentially of, based upon the weight of the powder, about 40% to 70% by weight ibuprofen, about 15% to 50% by weight of acetate phthalate cellulose and about 5% to 40% by weight colloidal silica, the powder having been spray dried from a suspension of the colloidal silica in a lower alkanol solution of the ibuprofen and the cellulose material, the lower alkanol being mixed with up to 50% ethyl acetate.

3. The taste neutral powder of claim 1 wherein the lower alkanol is isopropyl alcohol.

4. The dosage form of claim 2 wherein the lower alkanol is isopropyl alcohol.

5. In a pharmaceutical dosage form for oral administration as a solid chewable taste-neutral tablet containing ibuprofen, the improvement which comprises incorporating into such tablet as the pharmaceutical substance a therapeutic taste-neutral powder form of spray-dried ibuprofen which consists essentially of, based upon the weight of the powder, about 40% to 70% ibuprofen, about 15% to 50% by weight of cellulose acetate phthalate, and about 5% to 40% by weight cooloidal silica, the powder having been spray dried from a suspension of the colloidal silica in a lower alkanol solution of the ibuprofen and the cellulose acetate phthalate, the lower alkanol containing up to 50% ethyl acetate.

6. The dosage form of claim 5 wherein the lower alkanol is isopropyl alcohol.

* * * * *